United States Patent [19]

Mendes et al.

[11] Patent Number: 5,026,711
[45] Date of Patent: Jun. 25, 1991

[54] 4-AMINO QUINOLINES AND NAPHTHYRIDINES AND THEIR USE AS MEDICINES

[75] Inventors: Etienne Mendes, Toulouse; Jean-Claude Vernieres, Muret; Peter E. Keane, Garonne; André Bachy, Toulouse, all of France

[73] Assignee: Sanofi, Paris, France

[21] Appl. No.: 362,105

[22] Filed: Jun. 6, 1989

[30] Foreign Application Priority Data

Jun. 6, 1988 [FR] France ............................ 88 07498
Jun. 15, 1988 [FR] France ............................ 88 08075

[51] Int. Cl.$^5$ ............... A61K 31/435; A61K 31/47; C07D 215/54; C07D 471/04
[52] U.S. Cl. ................... 514/300; 514/183; 514/210; 514/234.5; 514/258; 514/291; 514/293; 514/313; 540/481; 540/597; 544/127; 544/362; 546/83; 546/90; 546/122; 546/123; 546/162
[58] Field of Search ............. 546/83, 90, 122, 123, 546/162; 544/127, 362; 514/300, 234.5, 253, 313, 183, 210, 291, 293; 540/481, 597

[56] References Cited

FOREIGN PATENT DOCUMENTS 0018735 11/1980 European Pat. Off. .
0205362 12/1986 European Pat. Off. .
0245054 11/1987 European Pat. Off. .
0259174 3/1988 European Pat. Off. .

OTHER PUBLICATIONS

Wastek et al., Eur. J. of Pharmacology, vol. 50, pp. 445–447, (1978).
Cyrus J. Ohnmacht et al., "Antimalarials. 5. α-Dibutylaminomethyl- and α-(2-Piperidyl)-3-Quinolinemethanols" Journal of Medicinal Chemistry, 1971, vol. 14, No. 1, pp. 17–24.
"Heterocyclic Compounds (More Than One Hetero Atom)", Chemical Abstracts, vol. 97, No. 19, Nov. 8, 1982.

Primary Examiner—Bernard I. Dentz
Attorney, Agent, or Firm—Wegner, Cantor, Mueller & Player

[57] ABSTRACT

Compounds represented by the general formula:

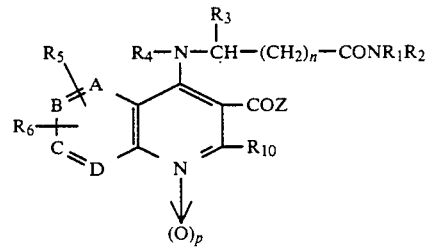

in which $R_1$ and $R_2$ are selected from hydrogen, $C_1$–$C_6$ alkyl or $C_2$–$C_6$ alkenyl, phenyl or benzyl or $R_1$ and $R_2$ form together with the nitrogen atom to which they are attached a $C_4$–$C_8$ saturated heterocycle, $R_3$ is selected from hydrogen, $C_1$–$C_6$ alkyl, phenyl or $C_7$–$C_9$ phenylalkyl, $R_4$ is selected from hydrogen or $C_1$–$C_4$ alkyl, $R_5$ and $R_6$ are selected from hydrogen or halogen, $C_1$–$C_3$ or alkoxy, nitro or trifluoromethyl; Z is selected from OH, $C_1$–$C_6$ alkoxy, $C_1$–$C_4$ alkyl, benzyl, $C_4$–$C_6$ aryl with or without a heteroatom, or $NR_8R_9$, $R_8$ and $R_9$ being selected from hydrogen, $C_1$–$C_4$ alkyl, phenyl or benzyl; $R_{10}$ is selected from hydrogen, $C_1$–$C_4$ alkyl or phenyl; n is 0, 1 or 3, p is 0 or 1 and one of the symbols A, B, C, D represents N and the others CH or A, B, C, D all represent CH and their acid addition salts, and their salts with bases. The compounds are useful in the prevention and treatment of cardiovascular diseases, as anti-allergic drugs, in the prevention and treatment of infectious states, and for the treatment of anxiety.

20 Claims, No Drawings

4-AMINO QUINOLINES AND NAPHTHYRIDINES AND THEIR USE AS MEDICINES

The present invention relates to novel derivatives of 4-amino quinolines and naphthyridines, a process for their preparation and their use in therapy.

Derivatives of the naphthyridines and especially of the quinolines are already known to be useful in therapy on account of very varied pharmacological activities such as antibacterial, antihypertensive, anxiolytic, antiinflammatory and analgesic activities which depend essentially on the groups substituting the aromatic ring. Some of these derivatives have been reported to bind to the benzodiazepine receptors; mention may be made for example of:

The 4-amino 3-carbamoyl quinolines described in EP-A-0 245 054 of formula A:

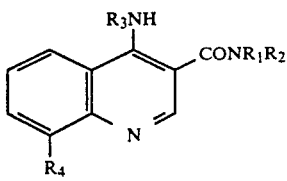

in which $R_1$, $R_2$, $R_3$, $R_4$ are selected from H or hydrocarbon groups: alkyl, aryl, aralkyl;

the quinolines described in FR-A-2 582 514 of formula B:

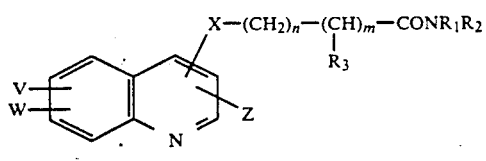

in which $R_1$, $R_2$, $R_3$, $R_4$ are selected from H or alkyl or aryl, Z is aryl and X is selected form $CH-R_4$, $N-R_4$, SO, $SO_2$, O or S and V and W are selected from H, halogen, alkyl, alkoxy, $NO_2$ or $CF_3$;

the naphthyridines described in EP-A-0 234 971 of formula C:

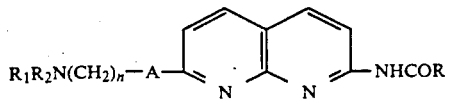

in which R is selected from cycloalkyl, heteroaryl, substituted or unsubstituted phenyl, A is selected from N, S, SO, or O and $R_1$, $R_2$ are selected in particular from H or alkyl;

the quinolines described in FR-A-2 581 382 of formula D:

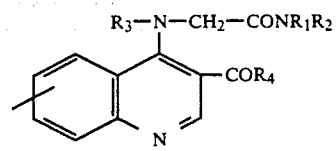

in which $R_1$, $R_2$, $R_3$ are selected from H, alkyl or aryl, and $R_4$ is selected from OH, alkoxy or alkyl.

Novel compounds have now been discovered which, at pharmacologically significant doses, do not bind to the central receptors of the benzodiazepines like those compounds just mentioned but which bind uniquely to the receptors of the peripheral type, the occupation of which is known to induce pharmacological activities different from those resulting from the activation of the central receptors.

The invention relates to compounds corresponding to formula I:

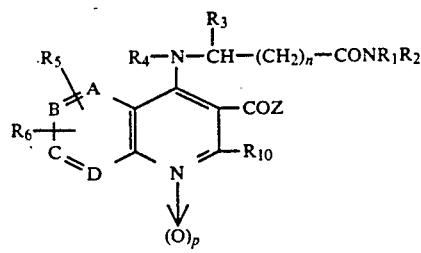

in which
$R_1$ and $R_2$, identical or different, is each selected from hydrogen, $C_1-C_6$ alkyl or $C_2-C_6$ alkenyl, phenyl or benzyl, or $R_1$ and $R_2$ form together with the nitrogen atom to which they are attached a $C_4-C_8$ saturated heterocyle, which may include a second heteroatom such as piperidine, pyrrolidine, morpholine, piperazine, $R_3$ is selected from hydrogen, $C_1-C_6$ alkyl, phenyl or $C_7-C_9$ phenylalkyl, $R_4$ is selected from hydrogen or $C_1-C_4$ alkyl, $R_5$ and $R_6$, identical or different, is each selected from hydrogen or halogen, $C_1-C_3$ alkyl or alkoxy, nitro, trifluoromethyl, or form together a methylenedioxy group, Z is $OR_7$ and $R_7$ is selected from hydrogen or $C_1-C_6$ alkyl; $NR_8R_9$ and $R_8$ and $R_9$, identical or different, is each selected from hydrogen, $C_1-C_4$ alkyl, phenyl or benzyl; $C_1$ or $C_4$ alkyl; benzyl; or $C_4-C_6$ aryl with or without a heteroatom as in the case of phenyl, pyridyl, pyrrolyl, furyl, thienyl or imidazolyl, $R_{10}$ is selected from hydrogen, $C_1-C_4$ alkyl or phenyl;
n is 0, 1 or 2; p is 0 or 1; and one of the symbols A, B, C, D represents N and the others CH or A, B, C, D each represents CH, with the proviso that when Z is not aryl or benzyl, $R_3$ is not H, as well as their addition salts with pharmaceutically acceptable acids or bases.

Among the acids, mention may be made of hydrohalogen, nitric, sulfuric and phosphoric acids or carboxylic acids such as acetic acid, formic acid, succinic acid, tartaric acid, oxalic acid and aspartic acid or sulfonic acids such as methanesulfonic acid or benzenesulfonic acid; the salts with bases may be alkali salts, alkaline earth salts or salts with amines such as lysine, piperazine or ethanolamine.

The alkyl groups may be straight, branched or cyclic.

The phenyl or benzyl groups may be substituted by halogens, $C_1-C_3$ alkoxy, alkyl or thioalkyl, nitro, trifluoromethyl or hydroxy.

When an asymmetric carbon occurs, the racemates and the stereoisomers are part of the invention.

Among the preferred products which are part of the invention mention may be made of quinoline or 1,5-naphthyridine esters of formula I in which $R_{10}$ is H, Z is $OR_7$ and $R_7$ is $C_1$-$C_3$ alkyl and more particularly ethyl, $R_3$ is $C_1$-$C_3$ alkyl and more particularly methyl, n is 0 and $R_4$ is H and preferably those in which the symbol C is substituted by an atom different from H as well as the compounds in which Z is aromatic or heteroaromatic, n is 0 and R is H and more particularly those in which $R_1$ is $C_1$-$C_4$ alkyl and $R_2$ is a phenyl ring substituted or not.

Another object of the invention is the process for the preparation of the compounds of formula I which consists of reacting the amine of formula II:

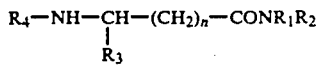

with the derivative of formula III

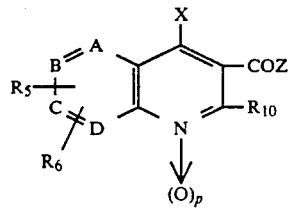

in which $R_1$, $R_2$, $R_3$, $R_4$, $R_5$, $R_6$, $R_{10}$, Z, A, B, C, D, n and p have the same meanings as in formula I and X is selected from halogen such as Cl or Br or sulfonate $RSO_3$ in which R is alkyl or benzyl.

The substitution of the amine II may be carried out under usual conditions at a temperature between 80° C. and 180° C., preferably in the presence of an organic or mineral base such as a tertiary amine or an alkali carbonate in order to bind the acid formed; the reaction is usually carried out in an organic solvent such as a hydrocarbon, for example toluene, an alcohol such as ethanol or isopropanol, an ether such as dioxane, or in a polar aprotic solvent such as dimethylformamide; the reaction may also be carried out at a pressure higher than atmospheric pressure and included between 5 and $70 \times 10^5$ Pa in a closed vessel; the reaction may also be carried out in a two-phase system in the presence of a phase transfer catalyst.

Some derivatives of formula II have already been described such as the 2-amino N,N-diethylpropanamide in J. Chem. Soc. p. 2972-2980 (1952). The others may be prepared starting from known substances by applying conventional methods and for example:

from amino acid derivatives IV, the amino function of which is protected as a labile carbamate and the acid function of which is activated in the form of a succinimidoyl or p-nitrophenylcarboxy group as described by G. W. Anderson in J. A. C. S. 86 p. 1839-1842 (1964):

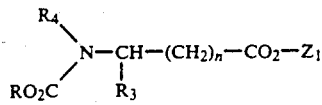

in which $Z_1$ represents succinimidyl or p-nitrophenyl, $R_3$, $R_4$ and n have the same meanings as in formula I and R is selected from $C_1$-$C_4$ alkyl, with which is reacted the amine $HNR_1R_2$ to form the compound of formula V:

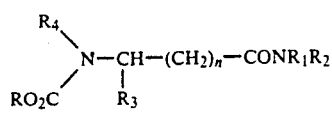

(in which $R_1$, $R_2$, $R_3$, $R_4$ and n have the same meanings as in formula I and R is alkyl) before the carboxyl group protecting the terminal amine is removed by the action of an acid such as trifluoroacetic, sulfuric or hydrochloric acids;

from amides of formula VI

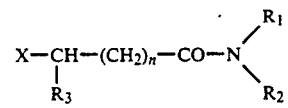

(in which X represents Cl or Br, and $R_1$, $R_2$, $R_3$ and n have the same meanings as in formula I) which may be prepared according to the process described in Synthetic Organic Chemistry-chap. 19; R. B. Wagner and H. D. Zook (1953), published by J. Wiley and Sons and in the case of n=o and $R_3$=H by the reaction of $HNR_1R_2$ on $ClCH_2COCl$, with which is then reacted the amine $R_4$-$NH_2$ at a temperature between 60° C. and 130° C. in solution in an alcohol or an ether at atmospheric pressure or at a pressure included between 5 and $40 \times 10^5$ Pa, optionally in the presence of a mineral or organic base; the process may be that described by J. B. M. Bettolo and J. F. Cavalla in Gazz. Chim. Ital. p. 896-907 (1954)

by a phtalimide intermediate of formula VII when $R_4$=H

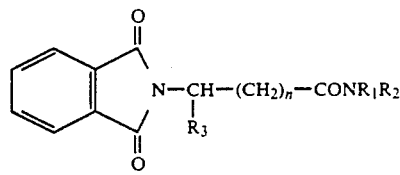

according to a method similar to that described by R. D. Haworth et al. in J. Chem. Soc. p. 2972-2980 (1952).

Certain starting quinolines or their corresponding derivatives hydroxylated at position 4 (formula III: A=B=C=D=CH; X=OH or Cl) are known compounds described in particular in J. Med. Chem. 22, 7 p. 816-823 (1979) or in FR-A-2 581 382, previously cited; and those in which $R_{10}$ is different from H may be prepared by the method described by R. P. Staiger and E. B. Miller in J. Org. Chem. 24 p. 1214 (1959).

The naphthyridines of formula III, in which X=OH and Z represents $OR_7$ may be prepared by conventional methods previously described, for example in Heterocyclic Compounds-vol. 7 (1961) : naphthyridines (Chap. 2) Ed. J. Wiley.

The new compounds of formula III in which X=OH and Z is selected from alkyl or aryl may be obtained by cyclization of compounds of formula VIII:

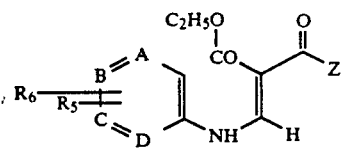

in which $R_5$, $R_6$, and A, B, C, D have the same meanings as in formula I, and Z is selected from $C_1-C_4$ alkyl, or $C_4-C_6$ aryl such as phenyl, furyl, thienyl, pyridyl, imidazolyl or pyrrolyl.

This cyclization may be carried out by heating compound VIII at a temperature between 180° C. and 310° C. in a high boiling solvent such as diphenyl or diphenyl ether or a mixture of them.

The cyclization can also be carried out by the reaction with sulfuric acid and acetic anhydride according to a method described by R. K. MAPARA, in J. Indian Chem. Soc., 1954, 31, 951, or by the reaction of a polyphosphoric ester (PPE) as described by H. AGUI, in J. Heterocyclic. Chem. 1971, 557.

The compounds of formula VIII may be obtained by reaction of an equimolar mixture of ethyl orthoformate, an aromatic amine and an ethyl acetate derivative according to the reaction scheme:

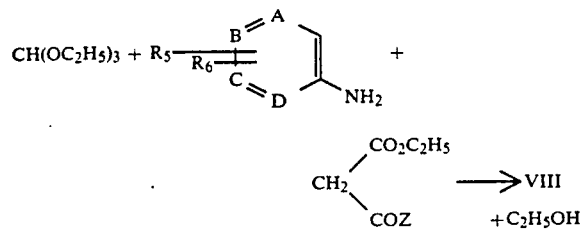

in which formulae $R_5$, $R_6$, Z and A, B, C, D have the same meanings as in formula VIII.

The reaction is usually carried out at a temperature between 80° and 160° C., preferably in a solvent, with the removal of ethanol as it is formed.

The compounds of formula VIII can also be prepared starting from the aromatic amine of the above scheme, with which is made to react ethyl orthoformate to give rise, in a known reaction, to a formamidine of formula:

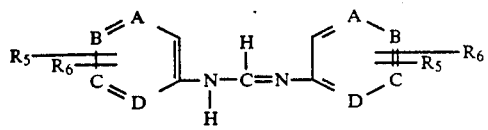

in which $R_5$, $R_6$ and A, B, C, D have the same meanings as in formula I and which form the product of formula VIII by reaction with the ethyl acetate derivative of the preceding scheme in the presence of an excess of ethyl orthoformate.

The compounds of formula III in which X represents a halogen are prepared in a conventional manner by reaction of the corresponding hydroxylated derivatives with $SOCl_2$, $POCl_3$ or $PCl_5$ when X=Cl or with $PBr_3$ or $POBr_3$ when X=Br, preferably in excess, at a temperature included between 60° C. and 190° C., where appropriate in a solvent such as dichloroethane, toluene or chlorobenzene.

The compounds of formula I which are N-oxides may be prepared starting from the N-oxides of the compounds of formula III in which X represents a halogen; these latter result from the reaction of a peracid with the amine according to a conventional method for example by the reaction of m-chloroperbenzoic acid on the quinoline or naphthyridine in solution in acetic acid.

The compounds of formula I in which Z=OH are obtained by the action of a base, for example an alkali carbonate in aqueous-alcoholic medium on the corresponding ester, followed by the recovery of the acid from its salt.

The compounds of formula I in which $Z=NR_8R_9$ are obtained by reaction of the amine $HNR_8R_9$ on the compound of formula I in which $Z=OR_7$, and preferably $OC_2H_5$, at a temperature between 60° C. and 120° C. without solvent or in a solvent such as dimethylformamide. They may also be formed starting from compounds of formula III in which X is a halogen and Z is Cl, which are reacted with $NH_3$ or the amine of formula $HNR_8R_9$ to obtain the compound of formula III in which Z is $NR_8R_9$, the compounds of formula I being then prepared in a conventional manner; some of the starting acid chlorides have been described in FR-A-2 581 382.

The enantiomers of the compounds of formula I can be prepared either from optically active amines of formula II, particularly when the amino-acids of formula

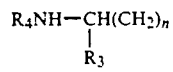

are commerically available, or by recrystallization of a salt of the racemic amine of formula I with an optically active acid such as the levo-rotatory or dextro-rotatory camphorsulfonic acids according to a known method.

The addition salts of the amine groups of compounds of formula I are prepared by reaction of a mineral or organic acid on the amine in solution and the salt is isolated either by evaporation of the solvent or by addition of a non-solvent to the solution.

The salts of the carboxylic acid are prepared by reaction of a mineral base such as NaOH or an organic base on the acid in solution.

The invention also relates to compositions containing at least one compound of formula I or one of its pharmaceutically acceptable salts.

These compounds have, in fact, an affinity in vitro and in vivo for the benzodiazepine receptors of the peripheral type without exhibiting specific affinity for the central benzodiazepine receptors.

It is known that the binders of these peripheral receptors have an action on the cardiovascular system as peripheral vasodilators which increase the coronary blood flow, they are immunomodulators or they can modify behavior, being anxiolytic.

Depending on the case, the compounds according to the invention can be used in human medicine, for the prevention and treatment of cardiovascular diseases or also as antiallergic drugs and in the prevention and treatment of infectious states or for the treatment of anxiety. To animals and particularly to beef cattle, pigs, sheep and goats, the compounds according to the invention may be administered for the prevention and treatment of infectious conditions, in particular by reinforcing their immune defenses.

The compounds of the invention may be administered to man for example by the oral route, in the form of tablets, capsules or granules, or by the rectal route in the form of suppositories or by the parenteral route in the form of an injectable solution in amounts varying from 1 mg to 400 mg per day, in one or more unit doses depending on the structure of the compound, the age of the patient and the nature and severity of the disease.

They may also be administered to animals incorporated in the feed or by injection at doses varying between 0.01 mg/kg/day and 100 mg/kg/day.

The compounds of formula I or their salts can be combined with usual carriers suitable in view of their chemical reactivity to give immediate- or sustained-release pharmaceutical forms.

The following examples illustrate the invention. The elementary analyses of the compounds obtained comply with the accepted norms. The products are characterized by their instant melting points, and, optionally, by their NMR spectrum (m signifies multiplet, d doublet, s singlet, t triplet and (x H) that the peak comprises X protons), the internal reference is $Si(CH_3)_4$); the infra red spectra show the characteristic bands of the expected structures. Unless there is special mention, p=O in the Examples.

1. Preparation of the amines of formula II:

(a) 2-amino-N,N-dipropylpropanamide (formula II: $R_1=R_2=C_3H_7$, $R_3=CH_3$, $R_4=H$, n=1)

58 g of N-(tert.butoxycarbonyl)alanine, prepared from racemic alanine, 33 g of N-hydroxysuccinimide and 59 g of dicyclohexylcarbodiimide dissolved in 1400 ml of dioxane are stirred for 6 hours. The precipitate is then separated and the solvent is evaporated under reduced pressure. The residue is washed with an aqueous solution of 5% $Na_2CO_3$.

After drying, 81 g of the compound of formula IV are isolated: ($R_3=CH_3$, $R_4=H$, $R=C_2H_5$, n=1) which melts at 143° C. (Starting from L-alanine, a product melting at 168° C. is obtained under the same conditions).

80 g of this product are dissolved in 700 ml of tetrahydrofuran containing 140 ml of dipropylamine and the mixture is stirred for 48 hours. The solvent is then evaporated under reduced pressure and, after washing with water and drying, 80 g are obtained of the compound of formula V in which $R_1=R_2=C_3H_7$, $R_3=CH_3$, $R_4=H$, $R=C_2H_5$, n=1, which melts at 92° C. (The product prepared from compound IV derived from L-alanine does not crystallize).

This compound is dissolved in 400 ml of chloroform; 160 ml of trifluoroacetic acid dissolved in 200 ml of chloroform are added at 5° C. and after being stirred for 3 hours, the solvent is evaporated under reduced pressure. Water is added to the residue and the solution is neutralized by the addition of NaOH before the expected product is extracted into di-chloromethane. 29 g of a yellow oil are thus obtained. $^1H$ NMR spectrum: (60 MHz, DMSOd$_6$) δ(ppm): 0.6–1.2(m, 9H); 1.2–1.8(m, 4H); 2.2–2.6(s, 2H replaceable); 3–3.4(m, 5H). (The amine derived from L-alanine or its trifluoroacetate is isolated in the same manner after evaporation of the chloroform).

(b) 2-amino-N,N-dibutyl propanamide:

7 g of the compound of formula IV, prepared as in (a), are dissolved in 100 ml of tetrahydrofuran containing 30 ml of N,N-dibutylamine; after being stirred for 30 hours the solvent is removed by distillation and the residue is washed with water to give 7.5 g of the product of formula V in which $R_1=R_2=C_4H_9$, $R_3=CH_3$, $R_4=H$, $R=C_2H_5$ and n=1, which melts at 80° C.

This product is dissolved in 100 ml of $CHCl_3$ containing 28 ml of $CF_3$—COOH at 0° C. and treated like its analog.

(c) 2-amino-N-methyl N-4-chlorophenylpropanamide:

17.6 ml of 2-chloro propionyl chloride are added slowly at 5° C. to a solution of 24.2 ml of N-methyl N-4-chlorophenylamine and 30 ml of triethylamine in 50 ml of ethyl ether; the mixture is stirred and allowed to return to ambient temperature; 5 hours after the end of the addition the precipitate is separated, the solvent is evaporated under reduced pressure and the residue is dissolved in ethyl ether; the organic solvent is washed with an aqueous solution of HCl (0.5N) then with water before the solvent is removed to give the product of formula VI in 55% yield, in which $R_1=CH_3$ $R_2=4$-$ClC_6H_4$, $R_3=CH_3$, n=o, X=Cl.

5 g of this compound are heated at 100° C. for 3 hours in an autoclave of 100 ml capacity containing 60 ml of liquid ammonia. After 12 hours, during which the reaction mixture returns to room temperature, the ammonia is removed and the desired amine is extracted with ethyl ether.

2.5 g of an oil are thus obtained. $^1H$ NMR (60 MHz, CDCl$_3$) δ: 1.1–1.2(d, 6H); 2–2.3(m, 2H replaceable 3.2(s, 3H); 3.3–3.6(m, 1H); 6.9–7.5(m, 4H).

(d) 2-amino 3-phenyl-N,N-dipropyl propanamide (formula II: $R_1=R_2=C_3H_7$, $R_3=CH_2C_6H_5$, $R_4=H$, n=o).

26.5 g of N-(tert.butoxycarbonyl)phenylalanine (m.p.=110° C.), prepared by reaction of ditert.butyldicarbonate on racemic phenylalanine, 11.5 g of N-hydroxysuccinimide, 20.6 g of dicyclohexylcarbodiimide are introduced into 500 ml of dioxane; after 4 hours stirring, the insoluble material is separated and the solvent is evaporated under reduced pressure. The corresponding product of formula IV is obtained, and melts at 138° C.

After reaction with 12 g of dipropylamine the corresponding product of formula V is obtained melting at 94° C., which by reaction with trifluoroacetic acid in chloroform gives rise to the trifluoroacetate of the desired amide of formula II, melting at 108° C., in an overall yield of 40%.

(e) 2-amino-N-methyl N-4-chlorophenylacetamide (formula II: $R_1=CH_3$, $R_2=4$-$ClC_6H_4$, $R_3=R_4=H$, n=o)

70.8 g of N-methyl 4-chloroaniline and 101 g of triethylamine are added simultaneously and dropwise between 0° and 5° C. to 111.5 g of N-phthaloylglycyl chloride in carbon tetrachloride. The triethylamine hydrochloride which precipitates is removed at the end of the reaction and washed twice with 100 ml of $CCl_4$. After drying of the organic solution and removal of the solvent, the phthalimide of formula VII is obtained in 95% yield and melts at 180° C. (isopropanol).

79.5 g of this compound is suspended in 1500 ml of a 0.16M solution of $N_2H_4 \cdot H_2O$ in $C_2H_5OH$ and the mixture is refluxed for 3 hours before the solvent is distilled off. The residue is taken up in 500 ml of 2N aqueous HCl and the reaction mixture is maintained at 50° C. for 2 hours. After filtration, the filtrate is evaporated to dryness and the residue is recrystallized from isopropanol (yield 75%). M.p.=186° C.

2. Preparation of the quinolines of formula III (1) 3-benzoyl 4,6-dichloro quinoline.

(a) Preparation of 3-benzoyl 6-chloro 4-hydroxy quinoline (III: R$_5$=6-Cl; R$_6$=H; R$_{10}$=H; Z=C$_6$H$_5$; A=B=C=D=CH; X=OH)

A mixture of 4-chloro aniline (25.5 g), ethyl orthoformate (33.3 ml) and ethyl benzoylacetate (34.6 ml) is heated at 165° C. until the alcohol formed has been completely distilled. The intermediate ethyl 3-(4-chloroanilino) 2-benzoyl acrylate is crystallized by the addition of petroleum ether. It is recrystallized from cyclohexane, m.p.=111° C. (yield 45%), then added to 150 ml of diphenyloxide heated at a temperature of 200° C.

The mixture is heated at 240° C. for 5 hours while slow distillation is carried out. After addition of petroleum ether, the crystals obtained are filtered off and dried in a vacuum, M.p.>260° C. (Yield 86%).

(b) Preparation of 3-benzoyl 4,6-dichloro quinoline (III: X=Cl; R$_5$=6-Cl; R$_6$=H; R$_{10}$H; Z=C$_6$H$_5$; A=B=C=D=CH)

2 g of 3-benzoyl 6-chloro 4-hydroxy quinoline are added in small portions under nitrogen to 10 ml of phosphoryl chloride. The solution is refluxed for 3 hours. After evaporation of the solvent, the residue is poured onto ice and the mixture is neutralized by the addition of sodium carbonate. The expected product is extracted with dichloromethane: crystals (isopropyl ether). M.p.=148° C. (Yield 48%).

The quinolines of formula III, in which X=Cl, R$_6$=H, mentioned in table I below have been prepared by the same method as above.

TABLE I

| Z | R$_5$ | F °C. |
|---|---|---|
| C$_6$H$_5$ | 7-F | 95 |
| C$_6$H$_5$ | 7-CF$_3$ | 97 |
| C$_6$H$_5$ | 6-Cl | 148 |
| C$_6$H$_5$ | 7-Cl | 121 |
| C$_6$H$_5$ | 8-Cl | 171 |
| C$_6$H$_5$ | 5-Cl | 135 |
| C$_6$H$_5$ | H | 130 |
| C$_6$H$_5$ | 6-OCH$_3$ | 147 |
| C$_5$H$_4$N-4 | 7-Cl | 132 |
| C$_5$H$_4$N-3 | 7-Cl | 134 |
| C$_6$H$_5$ | 7-Br | 134 |
| C$_6$H$_5$ | 6-Br | 140 |

(2) 3-benzoyl 4-chloro 6-methoxy quinoline (III: X=Cl, R$_5$=6-OCH$_3$, R$_6$=H; R$_{10}$=H; Z=C$_6$H$_5$, A=B=C=D=CH)

(a) bis(4-methoxyphenyl) formamidine 20 g of 4-methoxy aniline and 166 ml of ethyl orthoformate are heated at 150° C. for 2 hours. The alcohol formed is simultaneously distilled off. The formamidine is precipitated by the addition of pertroleum ether to the cooled reaction mixture. M.p.=114° C. (Yield 40%).

(b) ethyl 2-benzoyl 3-(4-methoxy anilino)acrylate (VIII: R$_5$=4-OCH$_3$; R$_6$=H; Z=C$_6$H$_5$; A=B=C=D=CH)

A mixture of bis(4-methoxyphenyl)formamidine (8 g), ethyl orthoformate (6.2 ml) and ethyl benzoylacetate (5.4 ml) is heated at 170° C. for 2 hours, the alcohol being distilled as it is formed. Heating is continued for 2 hours after a second addition of ethyl benzoylacetate (5.4 ml).

The expected product is purified by means of column chromatography by eluting with a mixture of cyclohexane+ethyl acetate (6/4) to give a clear oil (yield 60%).

(c) 3-benzoyl 4-hydroxy 6-methoxy quinoline (III: R$_5$=6-OCH$_3$; R$_6$=H; R$_{10}$=H; Z=C$_6$H$_5$; A=B=C=D=CH; X=OH)

10 g of ethyl 2-benzoyl 3-(4-methoxyanilino)acrylate are added to a 155 ml of diphenyloxide at 220° C. The reaction mixture is maintained at 245° C. for 20 mn while the ethanol formed is distilled off. The expected product is crystallized by the addition of petroleum ether to the cooled solution. M.p.=260° C. (Yield 50%).

(d) 2 g of 3-benzoyl 4-hydroxy 6-methoxy quinoline are added to 40 ml of phosphoryl chloride and the solution is refluxed for 3 hours. After being concentrated, the residue is poured onto ice. The solution is neutralized by the addition of sodium carbonate, the chlorinated derivative is extracted with dichloromethane. Crystals, M.p.=147° C. (Yield 85%).

(3) 4,6-dichloro 3-(4-chlorobenzoyl)quinoline (III: R$_5$=6-Cl; R$_6$=H; Z=4—ClC$_6$H$_4$; A=B=C=D=CH; X=Cl)

(a) 2 g of 4-chloroaniline, 2.27 g of ethyl orthoformate, 3.47 g of ethyl 4-chlorobenzoyl acetate (prepared according to Burton, J. Chem. Soc. 1928, 904), are heated for 4 hours while the ethanol is distilled off. The crude ethyl 3-(4-chloroanilino) 4-chloro 2-benzoylacrylate obtained is then added to 76 ml of diphenyl ether, the mixture is heated to 25° C. for 30 minutes. The 3-(4-chlorobenzoyl) 6-chloro 4-hydroxy quinoline is obtained in a yield of 53%. M.p. >260° C.

(b) 2.5 g of the preceding product are added to 25 ml of phosphoryl chloride.

The mixture is refluxed for 3 hours. After work-up, 4,6-dichloro 3-(4-chlorobenzoyl) quinoline is obtained, M.p.=170° C. (Yield 90%).

(4) 4,7-dichloro 3-isonicotinoyl quinoline (III: X=Cl; R$_5$=7-Cl; R$_6$=H; R$_{10}$=H; Z=4—C$_5$H$_4$N; A=B=C=D=CH)

(a) ethyl isonicotinoyl acetate:

Ethyl isonicotinate (20 g, 0.132 mole) is introduced into a suspension of sodium hydride (0.185 mole) in tetrahydrofuran (120 ml) and the mixture is refluxed. After addition of ethyl acetate (19.4 ml, 0.198 mole) reflux is continued over night. After hydrolysis and evaporation of the organic solvent, the aqueous phase is washed with ethyl acetate and acidified by the addition of acetic acid. After extraction with dichloromethane and evaporation of the organic solvent, the crystals obtained are dried in a vacuum. M.p.=70° C. (Yield 86%).

(b) Ethyl 3-(3-chloroanilino) 2-isonicotinoyl acrylate (VIII: R$_5$=3-Cl; R$_6$=H; Z=3—C$_5$H$_4$N; A=B=C=D=CH)

A mixture of bis(3-chlorophenyl)formamidine (5 g), ethyl isonicotinoyl acetate (3.64 g) and ethyl orthoformate (3.74 ml) is heated for 45 minutes at 140° C. before a second addition of ethyl isonicotinoyl acetate (3.64 g) is made; the reaction mixture is then heated for a further 2 hours at 150° C.

The expected product is purified by column chromatography on silica by eluting with a mixture cyclohexane/ethyl acetate (1/1), then recrystallized from a mixture of isopropyl ether/ethyl acetate (8/2), m.p.=93° C. (Yield 87%).

$^1$H NMR (80 MHz, CDCl$_3$) 0.8–1.2(t,3H) 3.8–4.2(q,2H) 7–7.5(m,6H) 8.4–8.8(m,3H) 12–12.5(d,1H exchangeable).

(c) 7-chloro 4-hydroxy 3-isonicotinoyl quinoline (III: R$_5$=7-Cl; R$_6$=H; R$_{10}$=H; Z=4—C$_5$H$_4$N; A=B=C=D=CH; X=OH) 5.3 g of ethyl 3-(3-chloroanilino) 2-isonicotinoyl acrylate are heated for 20 minutes at 250° C. in 85 ml of diphenyl ether. The crystals obtained on cooling are washed with petroleum ether, then recrystallized from dimethylacetamide. M.p. >260° C. (Yield 60%).

(d) 4,7-dichloro 3-isonicotinoyl quinoline 2.7 g of 7-chloro 4-hydroxy 3-isonicotinoyl quinoline are added under nitrogen to 60 ml of POCl$_3$ and refluxed for 5 hours. After being filtered off, the precipitate is poured onto ice. The aqueous solution is made alkaline with sodium carbonate before the chlorinated derivative is extracted into dichloromethane: crystals (isopropyl ether). M.p.=132° C. (Yield 53%).

3. Preparation of the naphthyridines of formula III (1) 3-benzoyl 4-chloro 1,5-naphthyridine (III: X=Cl; R$_5$=R$_6$=R$_{10}$=H; Z=C$_6$H$_5$; A=N; B=C=D=CH)

(a) ethyl 3-(3-pyridyl)amino 2-benzoyl acrylate (VIII: R$_5$=R$_6$=H; Z=C$_6$H$_5$; A=N; B=C=D=CH)

An equimolar mixture of 3-amino pyridine, ethyl orthoformate and ethyl benzoylacetate is heated for 3 hours at 125°-130° C. under a gentle stream of nitrogen. When the reaction is complete, the product is purified by column chromatography on silica (toluene-ethanol, 95-5). M.p.=115° C. (isopropyl ether) Yield 60%. $^1$H NMR (60 MHz CDCl$_3$+trifluoroacetic acid) δ:0.7–1.2(m,3H) 3.8–4.2(q,2H) 7.1–7.9(m,7H) 8.3–8.8(m,3H).

(b) 3-benzoyl 4-hydroxy 1,5-naphthyridine (III: R$_5$=R$_6$=H; R$_{10}$=H; Z=C$_6$H$_5$; A=N; B=C=D=CH; X=OH)

120 g of ethyl 3-(3-pyridyl)amino 2-benzoyl acrylate are cyclized in Dowtherm A (a mixture of 816 ml of diphenyloxide and 318 g of biphenyl) by heating at 245°-250° C. for 30 minutes. The compound which precipitates from solution on cooling to ambient temperature is filtered off and washed with petroleum ether. Yield 40%; m.p. >260° C.

(c) 3-benzoyl 4-chloro 1,5-naphthyridine (III: X=Cl; R$_5$=R$_6$=H; R$_{10}$=H; Z=C$_6$H$_5$; A=N; B=C=D=CH)

19.5 g of 3-benzoyl 4-hydroxy 1,5-naphthyridine are added to 200 ml of phosphorus oxychloride at reflux. Refluxing is maintained for 0.5 hour. When the reaction is complete, the excess phosphorus oxychloride is removed under reduced pressure and the oily residue is neutralized by the addition of concentrated aqueous NaOH. After extraction into dichloromethane, the organic phase is washed with water and then dried over magnesium sulfate. The product is recrystallized from cyclohexane. M.p.=119° C. (Yield 60%).

(2) ethyl 7-bromo 4-chloro 1,5-naphthyridine 3-carboxylate obtained by applying the previous method to the hydroxyl derivative; this product melts at 130° C.

(3) 3-benzoyl 4-chloro 2-methyl 1,5-naphthyridine (formula III: X=Cl; R$_5$=R$_6$=H; R$_{10}$=CH$_3$; Z=C$_6$H$_5$; A=N; B=C=D=CH; p=0)

(a) 3-benzoyl 4-hydroxy 2-methyl 1,5-naphtyridine ethyl 2-benzoyl 3-(3-pyridylamino)crotonate, prepared by condensation of ethyl 2-benzoyl 3-ethoxy crotonate and 3-amino pyridine, is cyclized in 55% yield by heating in Dowtherm according to the process previously described. M.p. >260° C. $^1$H NMR (80 MHz, DMSOd$_6$) δ:2.4(s,3H); 7.4–8.2(m,7H); 8.7–8.9(d,1H); 12.1–12.4(m,1H).

(b) 7 g of the preceding derivative are dissolved in 50 ml of toluene and 10 ml of POCl$_3$ are added dropwise at the reflux temperature of the solvent. Refluxing is continued for 30 minutes after the addition is complete and the solvents are evaporated. After neutralization and drying, the residue is found to melt at 120° C. Yield 40%.

(4) 3-benzoyl 4-chloro 1,6-naphthyridine (III: X=Cl; R$_5$=R$_6$=H; R$_{10}$=H Z=C$_6$H$_5$, A=C=D=CH, B=N)

28 g of 3-benzoyl 4-hydroxy 1,6-naphthyridine, m.p. >260° C., prepared from 4-aminopyridine by applying the method described previously for the preparation of 3-benzoyl 4-chloro 1,5-naphthyridine, are added to 300 ml of phosphorus oxychloride and the mixture is refluxed for 1 hour. After work-up, the expected compound is recrystallized from ethyl acetate. Yield 80%. $^1$H NMR (60 MHz, CDCl$_3$) δ:7.4–8(m,6H) 8.8–9(m,2H) 9.75(s,1H).

(5) 3-benzoyl 4,7-dichloro 1,8-naphthyridine (III: X=Cl; R$_5$=7-Cl; R$_{10}$=R$_6$=H; Z=C$_6$H$_5$, A=B=C=CH, D=N)

(a) 3-benzoyl 7-chloro 4-hydroxy 1,8-naphthyridine (III: R$_5$=7-Cl; R$_6$=R$_{10}$=H; Z=C$_6$H$_5$; A=B=C=CH, D=N; X=OH)

27.5 g of ethyl 3-[2-(5-chloropyridyl)] amino acrylate are added to a mixture of 185 ml of diphenyloxide and 65 g of biphenyl heated to 210° C. When the addition is complete, the temperature is raised to 240°-245° C. and maintained at this temperature for 2 hours. After cooling, the compound which precipitates is filtered off and washed with petroleum ether. (M.p. >260° C.). $^1$H NMR (80 MHz, DMSOd$_6$) δ:7.4–8(m,6H) 8.3–8.7(m,2H) 13–13.5(m,1H).

(b) 3-benzoyl 4,7-dichloro 1,8-naphthyridine;

9 g of 3-benzoyl 7-chloro 4-hydroxy 1,8-naphthyridine and 30 ml of phosphorus oxychloride are refluxed for 1 hour. The excess phosphorus oxychloride is removed by distillation under reduced pressure and the residue is dissolved in dichloromethane. This organic phase is washed with an aqueous solution of NaOH until it becomes neutral. After decantation and washing with water, the dichloromethane solution is dried over sodium sulfate, the concentrated. The product is crystallized from cyclohexane. M.p.=160° C. (Yield 66%). $^1$H NMR (60 MHz, CDCl$_3$) δ:7.4–7.9(m,6H) 8.5–8.7(d,1H) 9(s,1H).

(6) ethyl 4,7-dichloro 1,8-naphthyridine 3-carboxylate.

10 g of ethyl 7-chloro 4-hydroxy 1,8-naphthyridine 3-carboxylate and 100 ml of POCl$_3$ are refluxed for 1 hour, then the excess POCl$_3$ is removed by distillation and the residue, taken up in methylene chloride, is neutralized by the addition of a concentrated aqueous solution of NaOH. After drying and evaporation of the solvent the residue is purified by column chromatography on silica by eluting with a mixture of toluene and ethanol (98/2-v/v). After recrystallization from cyclohexane, the naphthyridine is found to melt at 134°-136° C.

(7) 3-benzoyl 4-chloro 1,7-naphthyridine (formula III: X=Cl; R$_5$=R$_6$=R$_{10}$=H; Z=C$_6$H$_5$; A=B=D=CH; C=N; p=0)

(a) The 7-oxide of 3-benzoyl 4-hydroxy 1,7-naphthyridine is prepared from 3-aminopyridine 1-oxide described by J. C. Murray and C. R. Hauser in J. Org. Chem. p. 2008-14 (1954), ethyl benzoylacetate and ethyl orthoformate according to the process described for 3-benzoyl 4-hydroxy 1,5-naphthyridine; this product is obtained in 70% yield, m.p. >260° C.

(b) 3-benzoyl 4-hydroxy 1,7-naphthyridine 6.5 g of the N-oxide previously prepared are introduced into 240 ml of concentrated acetic acid with 12.7 ml of acetic anhydride and 2 g of 10% palladized charcoal and the mixture is stirred at room temperature under an atmosphere of hydrogen until no more $H_2$ is absorbed. After filtration, the filtrate is evaporated to dryness and the residue, taken up in 300 ml of water, is neutralized by the addition of NaOH; the precipitate formed is isolated; the expected product is thus obtained in 85% yield and melts at 228° C.

(c) 2 g of this hydroxylated derivative are chlorinated by heating in 20 ml of $POCl_3$ at reflux for 45 minutes; the product isolated after evaporation of the excess $POCl_3$ and neutralization is purified by column chromatography on silica by eluting with a mixture of toluene and ethanol (99/1); the naphthyridine obtained in 60% yield melts at 123° C. $^1H$ NMR (80 MHz, $CDCl_3$) δ:7.4–7.9(m,5H); 8–8.2(d,1H); 8.7–8.9(d,1H); 9(s,1H); 10.6(s,1H).

(8) 3-benzoyl 4-chloro 1,5-naphthyridine 1-oxide (formula III: X=Cl; $R_5=R_6=R_{10}=H$; $Z=C_6H_5$; A=N; B=C=D=CH; p=1)

5.37 g of 3-benzoyl 4-chloro 1,5-naphthyridine and 3.8 g of m-chloroperbenzoic acid are stirred in 200 ml of glacial acetic acid for 4 days at ambient temperature. The acetic acid is then evaporated and the residue is taken up in 500 ml of methylene chloride; the organic phase is washed with a saturated solution of sodium bicarbonate, then with water; after being dried, the solvent is removed and the residue is purified by chromatography and recrystallized from toluene. M.p.=135° C. $^1H$ NMR (80 MHz, $CDCl_3$) δ:7.6–8.3(m,6H); 9–9.2(m,2H); 9.3–9.5(m,1H).

EXAMPLE 1 ethyl 4-[1-(N,N-dipropylcarbamoyl)ethylamino] 7-trifluoromethyl quinoline 3-carboxylate (formula I: $R_1=R_2=C_3H_7$; $R_3=CH_3$, $R_4=H$, p=0, $R_5=H$, $R_6$=7-$CF_3$, $R_{10}=H$, $Z=OC_2H_5$, A=B=C=D=CH) reference number; SR 26241.

A solution of 2.6 g of 2-amino-N,N-dipropyl propanamide, 3 g of ethyl 4-chloro 7-trifluoromethyl quinoline 3-carboxylate (m.p.=60° C.) and 2 ml of triethylamine in 100 ml of ethanol is heated at reflux temperature for 6 hours.

After removal of the solvent, the residue is taken up in water and dichloromethane. The organic phase is decanted, the solvent is evaporated and the residue purified by column chromatography on silica by eluting with isopropyl ether. After recrystallization from hexane, the desired product is obtained in a yield of 32%; m.p.=100° C. $^1H$ NMR (80 MHz, $CDCl_3$) δ:0.6–1(m,6H); 1.3–1.8(m,10H); 2.9–3.8 (m,4H); 4.3–4.7(q,2H); 4.9–5.3(m,1H); 7.5–8.35(m,3H); 9.2(s,1H); 9.5–9.7(d,1H replaceable).

EXAMPLES 2 TO 30 ester derivatives of quinoline

These examples of compounds of formula I in which A=B=C=D=CH, and n=p=0 are presented in table II; the compounds were prepared by applying the method described in example 1.

TABLE II

| EX N° | SR | $R_1$ | $R_2$ | $R_3$ | $R_4$ | $R_5$ | $R_6$ | Z | $R_{10}$ | M.p. °C. | $[\alpha]^{20}$ (C. SOLVENT) |
|---|---|---|---|---|---|---|---|---|---|---|---|
| 2 | 26399 | $C_3H_7$ | $C_3H_7$ | $CH_3$ | H | H | 5-Cl | $OC_2H_5$ | H | 94 | |
| 3 | 26058 | $C_3H_7$ | $C_3H_7$ | $CH_3$ | H | H | 6-Cl | $OC_2H_5$ | H | 59 | |
| 4 | 26274 | $C_3H_7$ | $C_3H_7$ | $CH_3$ | H | H | 6-Cl | $OC_2H_5$ | H | 170 (HCl) | −19 (1;$H_2$ |
| 5 | 26310 | $C_3H_7$ | $C_3H_7$ | $CH_3$ | H | H | 7-Cl | $OC_2H_5$ | H | 83 | |
| 6 | 26378 | $C_3H_7$ | $C_3H_7$ | $CH_3$ | H | H | 7-Cl | $OC_2H_5$ | H | 160 (HCl) | −0.9 (1; $CH_3$ |
| 7 | 26422 | $C_3H_7$ | $C_3H_7$ | $CH_3$ | H | H | 7-Cl | $OC_2H_5$ | H | 175 (HCl) | +1.9 (1; $CH_3$ |
| 8 | 26351 | $C_3H_7$ | $C_3H_7$ | $CH_3$ | H | H | 8-Cl | $OC_2H_5$ | H | 98 | |
| 9 | 26377 | $C_3H_7$ | $C_3H_7$ | $CH_3$ | H | H | 7-Br | $OC_2H_5$ | H | 160 (HCl.H20) | |
| 10 | 26421 | $C_3H_7$ | $C_3H_7$ | $CH_3$ | H | 6-$CH_3$ | 7-$CH_3$ | $OC_2H_5$ | H | 170 (HCl.H20) | |
| 11 | 26492 | $C_3H_7$ | $C_3H_7$ | $CH_3$ | H | 6-Cl | 7-Cl | $OC_2H_5$ | H | 106 | |
| 12 | 26357 | $C_3H_7$ | $C_3H_7$ | $CH_3$ | H | H | 6-$OCH_3$ | $OC_2H_5$ | H | 140 (maleate) | |
| 13 | 26522 | $C_3H_7$ | $C_3H_7$ | $CH_3$ | H | H | 7-$OCH_3$ | $OC_2H_5$ | H | 102 | |
| 14 | 25552 | $C_3H_7$ | $C_3H_7$ | $CH_3$ | H | | 6,7-$OCH_2O$ | $OC_2H_5$ | H | 130 (maleate, $H_2O$) | |
| 15 | 26426 | $C_3H_7$ | $C_3H_7$ | $CH_3$ | H | H | H | $OC_2H_5$ | H | 170 (maleate) | |
| 16 | 26487 | $C_3H_7$ | $C_3H_7$ | $CH_3$ | H | H | 6-cyclohexyl | $OC_2H_5$ | H | 100 | |
| 17 | 26449 | $C_3H_7$ | $C_3H_7$ | $CH_3$ | H | H | 7-Cl | $OC_4H_9$ | H | 84 | |
| 18 | 26454 | $C_2H_5$ | $C_2H_5$ | $CH_3$ | H | H | 7-Cl | $OC_2H_5$ | H | 100 | |
| 19 | 26362 | $C_4H_9$ | $C_4H_9$ | $CH_3$ | H | H | 7-$CF_3$ | $OC_2H_5$ | H | 140 | |
| 20 | 26423 | $CH_3$ | (4-Cl)—$C_6H_4$ | $CH_3$ | H | H | 7-Cl | $OC_2H_5$ | H | 146 | |
| 21 | 26306 | $C_3H_7$ | $C_3H_7$ | $C_2H_5$ | H | H | 7-$CF_3$ | $OC_2H_5$ | H | 60 | |
| 22 | 26258 | $C_3H_7$ | $C_3H_7$ | $CH_2C_6H_5$ | H | H | 7-$CF_3$ | $OC_2H_5$ | H | 95 | |
| 23 | 26319 | $C_3H_7$ | $C_3H_7$ | $CH_3$ | H | H | 6-Cl | $OC_2H_5$ | $CH_3$ | oil | |
| 24 | 26269 | $C_3H_7$ | $C_3H_7$ | $CH_3$ | H | H | 6-Cl | $OC_2H_5$ | $C_6H_5$ | 110 | |
| 25 | 26641 | $C_3H_7$ | $C_3H_7$ | $CH_3$ | H | 6-$OCH_3$ | 7-$OCH_3$ | $OC_2H_5$ | H | 160 (maleate, $H_2O$) | |
| 26 | 26920 | $C_3H_7$ | $C_3H_7$ | $CH_3$ | H | H | 7-F | $OC_2H_5$ | H | 88 | |
| 27 | 26619 | $C_3H_7$ | $C_3H_7$ | $CH_3$ | $CH_3$ | H | 7-Cl | $OC_2H_5$ | H | oil | |
| 28 | 26632 | $C_3H_7$ | $C_3H_7$ | $CH_3$ | H | H | 7-Cl | OH | H | >260 | |
| 29 | 26275 | $C_3H_7$ | $C_3H_7$ | $C_6H_5$ | H | H | 7-$CF_3$ | $OC_2H_5$ | H | 126 | |
| 30 | 26529 | $C_3H_7$ | $C_3H_7$ | $C_6H_5$ | H | H | 6-Cl | $OC_2H_5$ | H | 102 | |

EXAMPLE 31 ethyl 6-chloro
4-[1-(N,N-dipropylcarbamoyl)ethylamino]
1,5-naphthyridine 3-carboxylate (formula I:
$R_1=R_2=C_3H_7$, $R_3=CH_3$, $R_4=R_5=H$, $R_6=6$-Cl,
$R_{10}=H$, $Z=OC_2H_5$; $A=N$, $B=C=D=CH$; $n=p=0$)
reference number: SR 26293.

A solution of 2.7 g of ethyl 4,6-dichloro 1,5-naphthyridine 3-carboxylate, m.p.=114° C., 2.2 g of 2-amino-N,N-dipropylpropanamide hemisulfate and 3.1 ml of triethylamine in 30 ml of ethanol is maintained at its reflux temperature for 1 hour.

The solvent is then removed under reduced pressure and the residue is dissolved in 50 ml of dichloromethane; the organic solution is washed twice with 10 ml of water and then the solvent is removed after drying.

The residue is purified by column chromatography on silica by eluting with a mixture of toluene and ethanol (99/1).

After recrystallization from cyclohexane, the expected product melted at 133° C. $^1$H NMR (60 MHz, CDCl$_3$) δ:0.6-1(t,6H); 1.1-1.8(m,10H); 2.8-3.8(m,4H); 4.1-4.6(q,2H); 6.1-6.5(m,1H); 7.2-7.5(d,1H); 7.7-8(s,1H); 8.95(s,1H); 10.4-10.7(d,1H replaceable).

EXAMPLE 32 ethyl 6-chloro
4-[1-(N,N-dipropylcarbamoylmethyl)ethylamino]
1,5-naphthyridine 3-carboxylate (formula I:
$R_1=R_2=C_3H_7$, $R_3=CH_3$; $R_4=R_5=H$; $R_6=6$-Cl;
$R_{10}=H$; $Z=OC_2H_5$; $A=N$, $B=C=D=CH$; $n=1$;
$p=0$. Reference number: SR 26331

By applying the procedure described in example 31, the desired product is obtained in 37% yield and melts at 102° C. after recrystallization from ethyl acetate. $^1$H NMR (80 MHz, CDCl$_3$) δ:0.55-1.00(t,6H); 1.15-1.80(m,10H); 2.50-2.95(m,2H); 3.00-3.50(m,4H); 4.10-4.50(q,2H); 5.40-5.80(m,1H); 7.30-7.50(d,1H); 7.90-8.10(d,1H); 9.01(s,1H); 9.40-9.60(d,1H).

EXAMPLE 33 ethyl 7-bromo
4-[1-(N,N-dipropylcarbamoyl)ethylamino]
1,5-naphthyridine 3-carboxylate (formula I:
$R_1=R_2=C_3H_7$, $R_3=CH_3$, $R_4=R_5=R_{10}=H$,
$R_6=7$-Br, $Z=OC_2H_5$, $n=p=0$, $A=N$,
$B=C=D=CH$). Reference number SR 26579

3.01 g of ethyl 7-bromo 4-chloro 1,5-naphthyridine 3-carboxylate, 2.86 g 2-amino-N,N-dipropylpropanamide trifluoroacetate and 2.7 ml of triethylamine are dissolved in 50 ml of ethanol and the solution is refluxed for 1 hour. The solvent is evaporated; a solution of the residue in methylene chloride is washed with water and the solvent is evaporated.

After recrystallization from cyclohexane, the expected product melts at 96° C.

EXAMPLE 34 ethyl 7-chloro
4-[1-(N,N-dipropylcarbamoylmethyl)ethyl amino]
1,5-naphthyridine 3-carboxylate (formula I:
$R_1=R_2=C_3H_7$; $R_3=CH_3$; $R_4=R_5=R_{10}=H$;
$R_6=7$-Cl; $Z=OC_2H_5$; $A=N$, $B=C=D=CH$; $n=1$;
$p=0$)

Reference number SR 26869

By applying the procedure described in example 31, this ester is obtained in 40% yield and melts at 88° C. after recrystallization from pentane.

EXAMPLE 35 ethyl 7-chloro 4-[1-(N,N-dipropylcarbamoyl)ethyl amino] 1,8-naphthyridine 3-carboxylate (formula I:
$R_1=R_2=C_3H_7$, $R_3=CH_3$, $R_4=R_5=R_{10}=H$,
$R_6=7$-Cl, $Z=OC_2H_5$, $A=B=C=CH$, $D=N$,
$n=p=0$)

Reference number: SR 26493

3 g of ethyl 4,7-dichloro 1,8-naphthyridine 3-carboxylate, 2,5 g of 2-amino-N,N-dipropylpropanamide hemisulfate and 3,6 ml of triethylamine are introduced into 30 ml of isopropanol and the mixture is refluxed for 3 hours. The solvent is evaporated; the residue, dissolved in methylene chloride, is washed with water, then chromatographed on a column of silica by eluting with a mixture of cyclohexane/ethyl acetate (80/20). After recrystallization from ethyl ether, it melts at 93° C.

EXAMPLE 36

Ethyl 7-chloro 4-[N-methyl N-(4-chlorophenyl)carbamoylmethylamino] 1,8-naphthyridine 3-carboxylate (formula I: $R_1=CH_3$; $R_2=4$-ClC$_6$H$_4$;
$R_3=CH_3$; $R_4=R_5=R_{10}=H$; $R_6=7$-Cl, $Z=OC_2H_5$;
$A=B=C=CH$, $D=N$; $n=p=0$)

Reference number: SR 26555

Prepared in a yield of about 10% by applying the process described in example 35, this product melts at 206°-208° C. after recrystallization from ethanol.

EXAMPLE 37

3-benzoyl 6-chloro
4-[N,N-dipropylcarbamoylmethylamino]quinoline
(formula I: $R_1=R_2=C_3H_7$; $R_3=R_4=R_{10}=H$;
$R_5=6$-Cl; $Z=C_6H_5$; $n=p=0$; $A=B=C=D=CH$)

Reference number: SR 26199

2 g of 3-benzoyl 4,6-dichloro quinoline and 1.55 g of 2-amino-N,N-dipropyl acetamide hydrochloride, prepared according to Haworth et al., J. Chem. Soc., 1952, 2972, are refluxed for 4 hours in the presence of 2.2 ml of triethylamine in 50 ml of isopropanol. After concentration to dryness, the residual oil is dissolved in dichloromethane and the organic phase is washed with water.

The expected product can be purified by chromatography on silica gel (eluant: cyclohexane-ethyl acetate (1/1): clear yellow crystals are obtained. M.p.=109° C.-110° C. (Yield 46%). $^1$H NMR (80 MHz DM SOd$_6$) δ:0.6-0.8(t,6H); 1.3-1.7(m,4H); 2.9-3.3(m,4H); 4.1-4.3(d,2H); 7.4-7.9(m,8H); 8.4(s,1H); 8.5(t,1H, replaceable with D$_2$O).

EXAMPLES 38 TO 73

The compounds prepared starting from the quinolines of formula III in which Z is aryl and $R_6=R_{10}=H$, $n=p=0$, by applying the process described in example 37, are shown in the following table III:

TABLE III

| EX | REF. SR | $R_1$ | $R_2$ | $R_3$ | $R_4$ | $R_5$ | Z | M.p. °C. (salt) |
|---|---|---|---|---|---|---|---|---|
| 38 | 26290 | $C_3H_7$ | $C_3H_7$ | H | H | 7-Cl | $C_6H_5$ | 118 |
| 39 | 26307 | $C_3H_7$ | $C_3H_7$ | H | H | 8-Cl | $C_6H_5$ | 97 |
| 40 | 26303 | $C_3H_7$ | $C_3H_7$ | H | H | H | $C_6H_5$ | 93 |
| 41 | 26372 | $C_3H_7$ | $C_3H_7$ | H | H | 6-OCH$_3$ | $C_6H_5$ | 126 |
| 42 | 26483 | $C_2H_5$ | $C_2H_5$ | H | H | 6-Cl | $C_6H_5$ | 108 |
| 43 | 26485 | $C_2H_5$ | $C_2H_5$ | H | H | 7-Cl | $C_6H_5$ | 172 (maleate) |
| 44 | 26386 | $C_4H_9$ | $C_4H_9$ | H | H | 7-Cl | $C_6H_5$ | 106 |
| 45 | 26467 | $CH_3$ | $CH(CH_3)C_2H_5$ | H | H | 7-Cl | $C_6H_5$ | 168 (maleate) |
| 46 | 26412 | $CH_3$ | (Cl-4)$C_6H_4$ | H | H | 7-Cl | $C_6H_5$ | 126 |
| 47 | 26397 | $C_3H_7$ | (Cl-4)$C_6H_4$ | H | H | 7-Cl | $C_6H_5$ | 181 |
| 48 | 26226 | $C_3H_7$ | $C_3H_7$ | $CH_3$ | H | 6-Cl | $C_6H_5$ | 120 (HCl. ½H$_2$O) |
| 49 | 26385 | $C_3H_7$ | $C_3H_7$ | $CH_3$ | H | 7-Cl | $C_6H_5$ | 206 (HCl) |
| 50 | 26450 | $CH_3$ | (Cl-4)$C_6H_4$ | $CH_3$ | H | 7-Cl | $C_6H_5$ | 155 |
| 51 | 26294 | $C_3H_7$ | $C_3H_7$ | H | $CH_3$ | 6-Cl | $C_6H_5$ | 117 |
| 52 | 26304 | $C_3H_7$ | $C_3H_7$ | H | H | 6-Cl | (Cl-4)—$C_6H_4$ | 139 |
| 53 | 26439 | $C_3H_7$ | $C_3H_7$ | H | H | 7-Cl | $C_5H_4N$-4 | 162 |
| 54 | 26588 | $CH_3$ | (Cl-4)$C_6H_4$ | H | H | 7-Cl | $C_5H_4N$-4 | 198 |
| 55 | 26610 | $C_3H_7$ | $C_3H_7$ | H | H | 7-Cl | $C_5H_4N$-3 | 170 (maleate) |
| 56 | 26643 | $CH_3$ | (Cl-4)$C_6H_4$ | H | H | 7-Cl | $C_5H_4N$-3 | 105 |
| 57 | 26581 | $C_3H_7$ | $C_3H_7$ | H | H | 5-Cl | $C_6H_5$ | 217 |
| 58 | 26620 | $CH_3$ | (Cl-4)$C_6H_4$ | H | H | 6-Cl | $C_6H_5$ | 187 |
| 59 | 26644 | $C_3H_7$ | $C_3H_7$ | H | H | 6-Br | $C_6H_5$ | 104 |
| 60 | 26676 | $CH_3$ | (diCl-3,4)$C_6H_4$ | H | H | 7-Cl | $C_6H_5$ | 126 |
| 61 | 26706 | $CH_3$ | (Cl-4)$C_6H_4$ | H | H | 7-F | $C_6H_5$ | 206 |
| 62 | 26778 | $CH_3$ | (CF$_3$-4)$C_6H_4$ | H | H | 7-Cl | $C_6H_5$ | 204 |
| 63 | 26794 | $CH_3$ | (Cl-4)$C_6H_4$ | H | H | 7-CF$_3$ | $C_6H_5$ | 160 |
| 64 | 26841 | $CH_3$ | (Cl-4)$C_6H_4$ | H | $CH_3$ | 7-Cl | $C_6H_5$ | 145 |
| 65 | 26846 | $CH_3$ | (OCH$_3$-4)$C_6H_4$ | H | H | 7-Cl | $C_6H_5$ | 111 |
| 66 | 26876 | $CH_3$ | (Cl-4)$C_6H_4$ | H | H | 7-Br | $C_6H_5$ | 125 |
| 67 | 27195 | $CH_3$ | (OCH$_3$-4)$C_6H_4$ | H | H | 7-Br | $C_6H_5$ | 144 |
| 68 | 27196 | $CH_3$ | (OCH$_3$-4)$C_6H_4$ | H | H | 7-Cl | $C_6H_5$ | 153 |
| 69 | 27271 | $CH_3$ | (OC$_2$H$_5$-4)$C_6H_4$ | H | H | 7-Cl | $C_6H_5$ | 166 |
| 70 | 27778 | $CH_3$ | (Cl-4)$C_6H_4$ | H | H | 7-CH$_3$ | $C_6H_5$ | 110 |
| 71 | 27295 | $CH_3$ | (SCH$_3$-4)$C_6H_4$ | H | H | 7-Cl | $C_6H_5$ | 140 |
| 72 | 27307 | $CH_3$ | (OCH$_3$-2,4)$C_6H_3$ | H | H | 7-Cl | $C_6H_5$ | 170 |
| 73 | 26680 | $C_3H_7$ | $C_3H_7$ | $C_6H_5$ | H | 7-Cl | $C_6H_5$ | 165 |

EXAMPLE 74

3-carbamoyl 6-chloro 4-[1-(N,N-dipropylcarbamoyl)ethylamino]quinoline (formula I: $R_1=R_2=C_3H_7$; $R_3=CH_3$; $R_4=R_5=H$; $R_6=6$-Cl; $R_{10}=H$; $n=p=0$; $A=B=C=D=CH$)

Reference number: SR 27277 (hydrate).

(a) 3-carbamoyl 4,6-dichloro quinoline 3 g of 4,6-dichloro quinoline 3-carboxylic acid chloride prepared according to the method described in J. Med. Chem. 14 (1), p. 17–23, (1971), are dissolved in 80 ml of dioxane in which a stream of gaseous ammoniac is bubbled for 2 hours at the laboratory temperature. The precipitate of ammonium chloride is filtered off and the solvent evaporated. The residue is dissolved in methylene chloride and the organic phase is washed with water until neutrality and then dried. The crystals obtained after evaporation of the solvent are washed with isopropyl ether. M.p.=209° C. Yield 65%.

(b) 2 g of the preceding amide, 3.4 g of 2-amino-N,N-dipropylpropanamide and 3.5 of triethylamine in 50 ml of isopropanol are refluxed for 3 h. The solvent is evaporated, the residue is dissolved in methylene chloride and the organic phase is washed with water. After drying and eliminating the methylene chloride, the residue is recrystallized twice from ethyl acetate. M.p.=184° C. (monohydrate). Yield=40%.

EXAMPLE 75

3-benzoyl 4-[N,N-dipropylcarbamoylmethylamino]1,5-naphthyridine (formula I: $R_1=R_2=C_3H_7$; $R_3=R_4=R_5=R_6=R_{10}=H$; $n=p=0$; $Z=C_6H_5$; $A=N$; $B=C=D=CH$)

Reference number: SR 26278 (hydrate)

A solution of 1.075 g of 3-benzoyl 4-chloro 1,5-naphthyridine and 0.86 g of 2-amino-N,N-dipropylacetamide and 1.27 ml of triethylamine in 30 ml of ethanol is refluxed for 1.5 hours. After concentration to dryness, the residue is dissolved in dichloromethane and the organic phase is washed with water before being decanted and dried over magnesium sulfate.

The desired compound is purified by column chromatography on silica by eluting with a mixture of toluene/ethanol (99-1). M.p.=108° C. (diisopropyl ether) (Yield 45%). $^1$H NMR (60 MHz, DMSOd$_6$) δ:0.5-0.9(m,6H); 1.1-1.7(m,4H); 2.8-3.3(q,4H); 3.6(s,1H (hydrate); 4.2-4.3(d,2H); 7.4-7.9(m,6H); 8.1-8.5(m,2H); 8.7-8.9(d,1H); 9.3-9.8(m,1H exchangeable).

EXAMPLE 76

3-benzoyl 4-[N-methyl N-(4-chlorophenyl) carbamoylmethylamino]1,5-naphthyridine 1-oxide (formula I: $R_1=CH_3$; $R_2=$4-Cl $C_6H_4$; $R_3=R_4=R_5=R_6=R_{10}=H$; $n=0$; $p=1$; $Z=C_6H_5$; $A=N$; $B=C=D=CH$)

Reference number: SR 26838

A mixture of 1 g of 3-benzoyl 4-chloro 1,5-naphthyridine 1-oxide, 0.9 g of 2-amino-N-methyl N-4-chlorophenyl acetamide hydrochloride and 0.54 ml of triethylamine in 60 ml of ethanol is stirred for 15 hours at ambient temperature; the mixture is concentrated to dryness and the residue is taken up in methylene chloride. The final product is purified by column chromatography on silica by eluting with a mixture of toluene and ethanol (90/10, v/v) and recrystallized from toluene. M.p.=243° C. Yield 40%.

EXAMPLES 77 TO 117

The naphthyridines shown in the following table IV for which $R_6=R_{10}=H$, $p=0$ were prepared by applying the process described in example 75.

TABLE IV

| Ex | Ref. SR | Posit. N | R$_1$ | R$_2$ | R$_3$ | R$_4$ | R$_5$ | Z | n | M.p. °C. | RECRYST. SOLVENT |
|---|---|---|---|---|---|---|---|---|---|---|---|
| 78 | 26286 | A = N | C$_3$H$_7$ | C$_3$H$_7$ | H | H | 6-Cl | C$_6$H$_5$ | 0 | 128 | Ethyl acetate |
| 79 | 26494 | A = N | C$_3$H$_7$ | C$_3$H$_7$ | H | H | 7-Br | C$_6$H$_5$ | 0 | 114 | Cyclohexane |
| 80 | 26410 | B = N | C$_3$H$_7$ | C$_3$H$_7$ | H | H | H | C$_6$H$_5$ | 0 | 148 | toluene |
| 81 | 26332 | A = N | C$_5$H$_{11}$ | C$_5$H$_{11}$ | H | H | H | C$_6$H$_5$ | 0 | 88 | Ethyl acetate |
| 82 | 26528 | A = N | CH$_3$ | CH(CH$_3$)C$_2$H$_5$ | H | H | H | C$_6$H$_5$ | 0 | 134 | toluene |
| 83 | 26361 | A = N | H | C(C$_3$H$_7$)$_3$ | H | H | H | C$_6$H$_5$ | 0 | 186 | toluene |
| 84 | 26276 | A = N | CH$_3$ | (Cl-4)C$_6$H$_4$ | H | H | H | C$_6$H$_5$ | 0 | 184 | acetonitrile |
| 85 | 26336 | A = N | CH$_3$ | (Cl-4)C$_6$H$_4$ | H | H | 6-Cl | C$_6$H$_5$ | 0 | 208 | Ethyl acetate |
| 86 | 26516 | A = N | CH$_3$ | (Cl-4)C$_6$H$_4$ | H | H | 7-Br | C$_6$H$_5$ | 0 | 204 | toluene |
| 87 | 26409 | B = N | CH$_3$ | (Cl-4)C$_6$H$_4$ | H | H | H | C$_6$H$_5$ | 0 | 217 | toluene |
| 88 | 26411 | A = N | C$_3$H$_7$ | (Cl-4)C$_6$H$_4$ | H | H | H | C$_6$H$_5$ | 0 | 173 | |
| 89 | 26359 | A = N | C$_3$H$_7$ | C$_3$H$_7$ | CH$_3$ | H | H | C$_6$H$_5$ | 1 | 115 | cyclohexane |
| 90 | 26455 | A = N | CH$_3$ | (Cl-4)C$_6$H$_4$ | CH$_3$ | H | H | C$_6$H$_5$ | 0 | 189 | toluene |
| 91 | 26517 | D = N | CH$_3$ | (Cl-4)C$_6$H$_4$ | CH$_3$ | H | 7-Cl | C$_6$H$_5$ | 0 | 192-94 | ethanol |
| 92 | 26554 | D = N | CH$_3$ | (Cl-4)C$_6$H$_4$ | H | H | 7-Cl | C$_6$H$_5$ | 0 | 209 | ethanol |
| 93 | 26360 | A = N | C$_3$H$_7$ | C$_3$H$_7$ | H | CH$_3$ | H | C$_6$H$_5$ | 0 | 146 | Ethyl acetate |
| 94 | 27303 | A = N | C$_2$H$_5$ | (F-2)(Cl-4)C$_6$H$_3$ | H | H | H | C$_6$H$_5$ | 0 | 155 | cyclohexane |
| 95 | 26871 | A = N | H | (Cl-4)C$_6$H$_4$ | H | H | H | C$_6$H$_5$ | 0 | 210 | toluene |
| 96 | 26858 | A = N | C$_2$H$_5$ | (Cl-4)C$_6$H$_4$ | H | H | H | C$_6$H$_5$ | 0 | 160 | ethanol |
| 97 | 26919 | C = N | CH$_3$ | (Cl-4)C$_6$H$_4$ | H | H | H | C$_6$H$_5$ | 0 | 165 | toluene |
| 98 | 27297 | A = N | CH$_3$ | (Cl-4)C$_6$H$_4$ | H | H | H | (OH-4)C$_6$H$_4$ | 0 | 182 | acetonitrile |
| 99 | 26830 | A = N | CH$_3$ | (Cl-4)C$_6$H$_4$ | H | H | 7-Cl | C$_6$H$_5$ | 0 | 195 | toluene |
| 100 | 26698 | A = N | CH$_3$ | (Cl-4)C$_6$H$_4$ | H | H | 6-OCH$_3$ | C$_6$H$_5$ | 0 | 247 | toluene |
| 101 | 26640 | D = N | CH$_3$ | (Cl-2)C$_6$H$_4$ | H | H | 7-Cl | C$_6$H$_5$ | 0 | 120 | cyclohexane |
| 102 | 26651 | A = N | CH$_3$ | (Cl-2)C$_6$H$_4$ | H | H | H | C$_6$H$_5$ | 0 | 132 | cyclohexane |
| 103 | 26847 | A = N | CH$_3$ | (CF$_3$-4)C$_6$H$_4$ | H | H | H | C$_6$H$_5$ | 0 | 220 | toluene |
| 104 | 27161 | A = N | CH$_3$ | (CH$_3$O-4)C$_6$H$_4$ | H | H | H | C$_6$H$_5$ | 0 | 150 | cyclohexane |
| 105 | 26980 | A = N | CH$_3$ | (CH$_3$-4)C$_6$H$_4$ | H | H | H | C$_6$H$_5$ | 0 | 175 | cyclohexane |
| 106 | 26803 | A = N | CH$_3$ | C$_6$H$_5$ | H | H | H | C$_6$H$_5$ | 0 | 105 | cyclohexane |
| 107 | 26731 | A = N | CH$_3$ | (Cl-4)C$_6$H$_4$ | H | H | H | C$_6$H$_5$ | 1 | 165 | toluene |
| 108 | 26710 | A = N | CH$_3$ | (Cl-4)C$_6$H$_4$ | H | CH$_3$ | H | C$_6$H$_5$ | 0 | 90 | petroleum ether |
| 109 | 26578 | D = N | CH$_3$ | (Cl-4)C$_6$H$_4$ | H | CH$_3$ | 7-Cl | C$_6$H$_5$ | 0 | 198 | ethanol |
| 110 | 27181 | A = N | CH$_2$—CH=CH$_2$ | (Cl-4)C$_6$H$_4$ | H | H | H | C$_6$H$_5$ | 0 | 160 | cyclohexane |

TABLE IV-continued

| Ex | Ref. SR | Posit. N | $R_1$ | $R_2$ | $R_3$ | $R_4$ | $R_5$ | Z | n | M.p. °C. | RECRYST. SOLVENT |
|---|---|---|---|---|---|---|---|---|---|---|---|
| 111 | 27153 | A = N | $CH_3$ | $(Cl-4)C_6H_4$ | H | H | H | $(CH_3O-4)C_6H_4$ | 0 | 165 | benzene |
| 112 | 26918 | A = N | $CH_3$ | $(Cl-4)C_6H_4$ | H | H | 6,7-Cl | $C_6H_5$ | 0 | 163 | ethanol |
| 113 | 26708 | A = N | $CH_3$ | $(Cl-3,4)C_6H_3$ | H | H | H | $C_6H_5$ | 0 | 176 | cyclohexane |
| 114 | 26972 | A = N | $CH_3$ | $(Cl-2,4)C_6H_3$ | H | H | H | $C_6H_5$ | 0 | 154 | cyclohexane |
| 115 | 26947 | A = N | $CH_3$ | $(Cl-2,6)C_6H_3$ | H | H | H | $C_6H_5$ | 0 | 195 | ethanol |
| 116 | 27249 | A = N | $CH_3$ | cyclohexyl | H | H | H | $C_6H_5$ | 0 | 185 | ethanol |
| 117 | 27252 | A = N | $CH_3$ | $(F-2Cl-4)C_6H_3$ | H | H | H | $C_6H_5$ | 0 | 138 | cyclohexane |

The compounds of the preceding examples are only slightly toxic, and in the mouse their $LD_{50}$ by the oral route is usually higher than 1000 mg/kg; thus, that of the compound of example 1 is 1100 mg/kg and that of example 84 is greater than 1800 mg/kg. The compounds of Examples 3, 67, 90, 107 and 114 are atoxic at the dose of 500 mg/kg in the mouse.

A study has also been made of their in vitro affinity for central benzodiazepine receptors and for those of the peripheral type according to the methods described in what follows: the $IC_{50}$ in vitro has been determined, i.e. the concentration in the medium of the studied product which inhibits 50% of the binding to the benzodiazepine receptors of a binder known to be specific for these receptors. The results obtained show that the products of the invention have a specific affinity for the receptors of the peripheral type but do not bind to the central receptors.

The methods used were the following:

(a) determination of the concentration of the product studied inhibiting 50% of the specific binding to the receptors of the peripheral type of 1-(2-chlorophenyl) 3-(N-methyl N-methylpropyl) carbamoyl isoquinoline (or PK 11195), known binder for these receptors.

The method is similar to that described by J. Benavides et al. in Brain Res. Bull. 13 p. 69–77 (1984) and references cited therein.

Suspensions of membrane proteins of cat brain were prepared as described by J. Benavides.

The assays of inhibition of the binding of [$^3$H] PK11195 to the receptors by the products to be tested were performed at 4° C. on 2 ml of suspension containing 0.05 mg of proteins and 0.5 nM of [$^3$H] PK11195; the incubations lasted 2h30.

Non specific binding was defined as the amount of [$^3$H] PK11195 displaced from the receptor by 10 μM of 7-chloro 1,3-dihydro 1-methyl 5-(4-chlorophenyl) 1,4-2H-benzodiazepine 2-one or RO 5-4864, another known binder.

The concentrations of the product to be tested inhibiting 50% of the specific binding of PK11195 to the receptor ($IC_{50}$) were calculated by means of the logit-log described by Finney in Probit analysis-Cambridge University Press, 1979.

(b) determination of the concentration of the product under study inhibiting 50% of the specific binding of flunitrazepam to the central receptors.

The brains of rats were removed after decapitation and ground, then placed in suspension in an aqueous solution of sucrose (0.32M). The mixture is centrifuged and the pellet is resuspended to give a homogenous suspension in a TRIS-HCl buffered solution (50 mM; pH=7.4). Aliquots of this suspension are incubated at 4° C. after addition of [$^3$H] flunitrazepam, alone or with increasing amounts of the compound to be tested. The amount of labelled product bound to the membranes after the latter have been separated from the incubation medium by binding to glass fiber filters is determined by means of liquid scintillation counting and the $IC_{50}$ is calculated by means of the logit-log method; non-specific binding of flunitrazepam is determined by introducing 2 μM of clonazepam.

The results of these assays for representative compounds of the invention are shown in table V.

TABLE V

| SR | $IC_{50}$ (nM) (peripheral) | $IC_{50}$ (nM) (central) |
|---|---|---|
| 26241 | 3 | >20000 |
| 26399 | 7 | 12700 |
| 26310 | 1 | >20000 |
| 26351 | 6 | 30000 |
| 26377 | 1 | >20000 |
| 26421 | 5 | 53000 |
| 26492 | 1 | >20000 |
| 26522 | 11 | >20000 |
| 26552 | 31 | 12400 |
| 26487 | 39 | >20000 |
| 26378 | 1 | >20000 |
| 26579 | 1 | >20000 |
| 26493 | 12 | >20000 |
| 26449 | 1 | >20000 |
| 26362 | 3 | >20000 |
| 26423 | 1 | 12600 |
| 26306 | 11 | >20000 |
| 26319 | 8 | 14000 |
| 26269 | 16 | >20000 |
| 26641 | 356 | >20000 |
| 26920 | 18 | >20000 |
| 26619 | 132 | >20000 |
| 26632 | 101 | >20000 |
| 26869 | 172 | >20000 |
| 26555 | 5 | >20000 |
| 26275 | 22 | >20000 |
| 26529 | 16 | >20000 |
| 26581 | 43 | >10000 |
| 26620 | 2.8 | >10000 |
| 26676 | 1.1 | >10000 |
| 26706 | 4 | >10000 |
| 26778 | 27 | >10000 |
| 26794 | 11 | >10000 |
| 26841 | 17 | >10000 |
| 26846 | 2.9 | >10000 |
| 26876 | 0.5 | >10000 |
| 27195 | 1 | >10000 |
| 27196 | 0.8 | >10000 |
| 27271 | 68 | >10000 |
| 26199 | 13 | 1640 |
| 26290 | 10 | >10000 |
| 26307 | 175 | >10000 |
| 26286 | 6 | 5480 |
| 26494 | 2 | 13000 |
| 26485 | 40 | >10000 |
| 26386 | 16 | >10000 |
| 26332 | 29 | >10000 |
| 26361 | 16 | >10000 |
| 26276 | 0.3 | 13400 |
| 26336 | 0.3 | 2120 |

TABLE V-continued

| SR | IC$_{50}$ (nM) (peripheral) | IC$_{50}$ (nM) (central) |
|---|---|---|
| 26409 | 84 | >10000 |
| 26554 | 28 | >10000 |
| 26412 | 0.4 | >10000 |
| 26397 | 4 | >10000 |
| 26226 | 4 | 11800 |
| 26450 | 2 | >10000 |
| 26455 | 1 | >10000 |
| 26517 | 27 | >10000 |
| 26360 | 89 | >10000 |
| 26304 | 13 | 14500 |
| 26439 | 89 | >10000 |
| 26588 | 2.1 | >10000 |
| 26610 | 35 | >10000 |
| 26643 | 1.2 | >10000 |
| 26858 | 0.77 | >10000 |
| 26919 | 52 | >10000 |
| 26554 | 28 | >10000 |
| 26830 | 0.13 | >10000 |
| 26698 | 1.95 | >10000 |
| 26878 | 246 | >10000 |
| 26640 | 46 | 3550 |
| 26651 | 0.93 | 8490 |
| 26847 | 1.59 | >10000 |
| 27161 | 2.3 | >10000 |
| 26980 | 1.31 | 9750 |
| 26803 | 7.1 | 5430 |
| 26731 | 2.74 | >10000 |
| 26710 | 3.2 | >10000 |
| 26578 | 330 | 48900 |
| 27181 | 0.89 | >10000 |
| 27153 | 1.62 | 47900 |
| 26918 | 0.16 | 1680 |
| 26708 | 2.8 | >10000 |
| 26947 | 0.79 | 18600 |
| 26838 | 10.8 | 7650 |
| PK11195 | 1.3 | 21400 |
| R05-4864 | 44 | inactive |
| DIAZEPAM | 523 | 11 |
| CHLORDIAZEPOXIDE | inactive | 654 |

The in vivo affinity for the receptors of the peripheral type of some of the compounds of the invention has also been studied. The assays were carried out in the mouse by using the binder [$^3$H] PK11195.

The products to be tested are administered orally in suspension in an aqueous solution of carboxymethylcellulose (1% wt/v) to groups of 4 mice 35 mn before the intravenous injection of [$^3$H] PK11195 at a concentration of 200 μCi/kg (specific activity 66 Ci/mmole). 5 mn after the injection the animals are sacrificed by decapitation and the different organs are removed and ground in 10 ml Tris-HCl buffer (50 mM; pH=7.4) to give homogenates.

The control groups only received the carboxymethylcellulose solution and the injection of [$^3$H] PK11195.

A determination was made for each organ by means of scintigraphy of:

1—the amount of radioactive binder present in an organ by measuring the radioactivity of an aliquot of the homogenate.

2—the amount of radioactive binder bound to the membrane tissues of an organ by measuring the radioactivity bound on a fiber glass filter after filtration of another aliquot of the homogenate.

3—the amount of radioactive binder bound non-specifically to the membrane tissues by incubating a control homogenate with an excess of RO5-4864, a known binder, followed by binding of the membranes to a filter and measurement of the radioactivity remaining on the membranes.

The inhibition of specific binding, recorded as SB, is equal to the difference between the radioactivity measurements 2 and 3 divided by measurement 1.

The percentages of inhibition of the binding in different organs determined for compounds of the invention and the reference substances are shown in table VI; they are given by the formula:

$$100 \times \frac{SB \text{ (control)} - SB \text{ (product)}}{SB \text{ (control)}}$$

TABLE VI

| SR No | Dose (mg/kg) | % Inhibition | | | | |
|---|---|---|---|---|---|---|
| | | brain | spleen | thymus | kidney | heart |
| 26310 | 25 | 76 | 52 | 31 | 32 | 39 |
| 26276 | 8 | 78 | 37 | 34 | 69 | 30 |
| 26830 | 25 | 64 | 26 | nd | nd | nd |
| 26412 | 25 | 79 | 62 | nd | nd | nd |
| 26876 | 25 | 84 | 64 | nd | nd | nd |
| 26858 | 25 | 95 | 84 | nd | nd | nd |
| 27161 | 25 | 92 | 78 | nd | nd | nd |
| 26846 | 25 | 91 | 80 | nd | nd | nd |
| 27153 | 25 | 87 | 52 | nd | nd | nd |
| PK 11195 | 15 | 71 | 29 | 30 | 54 | 27 |
| R05-4854 | 15 | 74 | 11 | 28 | 73 | 27 | nd = not determined

We claim:

1. A compound of formula I:

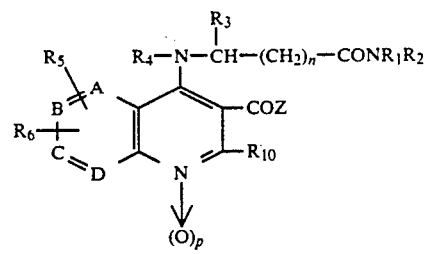

in which

R$_1$ and R$_2$, identical or different, is each selected from hydrogen, C$_1$-C$_6$ alkyl or C$_2$-C$_6$ alkenyl, phenyl or benzyl, or R$_1$ and R$_2$ form together with the nitrogen atom to which they are attached a C$_4$-C$_8$ saturated heterocycle, R$_3$ is selected from hydrogen, C$_1$-C$_6$ alkyl, phenyl or C$_7$-C$_9$ phenylalkyl, R$_4$ is selected from hydrogen or C$_1$-C$_4$ alkyl, R$_5$ and R$_6$, identical or different, is each selected from hydrogen or halogen, C$_1$-C$_3$ alkyl or alkoxy, nitro or trifluoromethyl, or form together a methylenedioxy group, Z is OR$_7$ in which R$_7$ is selected from hydrogen or C$_1$-C$_6$ alkyl; NR$_8$R$_9$ in which R$_8$ and R$_9$ is each selected from hydrogen, C$_1$-C$_4$ alkyl, phenyl or benzyl; benzyl; C$_4$-C$_6$ aryl with or without a heteroatom or imidazolyl R$_{10}$ is selected from hydrogen, C$_1$-C$_4$ alkyl or phenyl, with the proviso that when Z is not benzyl or aryl, R$_3$ is not H, the phenyl and benzyl groups may be substituted by halogen, C$_1$-C$_3$ alkoxy, alkyl or thioalkyl, nitro, trifluoromethyl or hydroxy, the alkyl and alkoxy groups being straight, branched or cyclic;

n is 0, 1 or 2, p is 0 or 1 and one of the symbols A, B, C, D is N and the others CH or A, B, C, D each represents CH, in the form of a racemate or enantiomers, as well as their addition salts with pharmaceutically acceptable acids or bases.

2. A compound according to claim 1, corresponding to formula I in which Z is a substituted or unsubstituted phenyl group.

3. A compound according to claim 2 in which Z is an unsubstituted phenyl group.

4. A compound according to claim 1, corresponding to formula I in which Z is pyridyl, pyrrolyl, furyl, thienyl or imidazolyl.

5. A compound according to claim 1, corresponding to formula I in which Z is $OR_7$.

6. A compound according to claim 5 in which $R_7$ is selected from alkyl.

7. A compound according to claim 1 of formula I in which A, B, C and D each represents CH.

8. A compound according to claim 1 of formula I in which one of the symbols A, B, C or D is N.

9. A compound according to claim 8 in which A is N.

10. A compound according to claim 1 of formula I in which $R_1$ and $R_2$ is each selected from $C_1$-$C_6$ alkyl, $R_3$ is selected from $C_1$-$C_3$ alkyl, $R_{10}$ is hydrogen and Z is $OR_7$ with $R_7$ being selected from $C_1$-$C_6$ alkyl.

11. A compound according to claim 10 in which $R_4$ is hydrogen.

12. A compound according to claim 10 in which $R_4$ is hydrogen and the symbol C is substituted.

13. A compound according to claim 1 of formula I in which $R_1$ is selected from alkyl, $R_2$ and Z each being selected from phenyl which may be substituted.

14. A compound according to claim 1 of formula I in which $R_1$ is selected from alkyl, $R_2$ and Z is phenyl which may be substituted, $R_3$ and $R_{10}$ each represent hydrogen.

15. A compound according to claim 13, wherein the symbols A, B, C and D each represents CH.

16. A compound according to claim 13, wherein the symbol A represents N and B, C and D represent CH.

17. Ethyl 7-chloro 4-[1-(N,N-dipropylcarbamoyl)ethylamino] quinoline 3-carboxylate and its addition salts with pharmacologically acceptable acids.

18. 3-benzoyl 7-chloro 4-(N-methyl N-4-chlorophenyl)carbamoyl methylamino quinoline and its addition salts with pharmacologically acceptable acids.

19. 3-benzoyl 4-(N-methyl N-4-chlorophenyl)carbamoylmethylamino 1,5-naphthyridine and its addition salts with pharmacologically acceptable acids.

20. Pharmaceutical composition comprising as active ingredient a compound according to claim 1 as well as a compatible carrier.

* * * * *

UNITED STATES PATENT AND TRADEMARK OFFICE
CERTIFICATE OF CORRECTION

PATENT NO. : 5,026,711

DATED : June 25, 1991

INVENTOR(S) : Etienne MENDES et al.

It is certified that error appears in the above-identified patent and that said Letters Patent is hereby corrected as shown below:

On the title page:

Item [30] "Foreign Application Priority Data," change "88 08075" to --88 08025--.

Signed and Sealed this

Twenty-ninth Day of December, 1992

*Attest:*

DOUGLAS B. COMER

*Attesting Officer*　　*Acting Commissioner of Patents and Trademarks*